United States Patent

Szántay et al.

[11] 4,429,129
[45] Jan. 31, 1984

[54] 1α-ETHYL-1β-(2'-ALKOXY CARBONYL-2'-HYDROXYIMINOETHYL)-10-METHOXY 1,2,3,4,6,7,12,12β-OCTAHYDROINDOLO(2,3a)QUINOLIZINES

[75] Inventors: Csaba Szántay; Lajos Szabó; György Kalaus; Tibor Keve; Lajos Dancsi, all of Budapest; János Galambos, Erd; Ferenc Vezekényi; Tibor Ács, both of Budapest, all of Hungary

[73] Assignee: Richter Gedeon Vegyészeti Gyár Rt, Budapest, Hungary

[21] Appl. No.: 410,052

[22] Filed: Aug. 20, 1982

[30] Foreign Application Priority Data

Aug. 23, 1982 [HU] Hungary ............... 2436/81

[51] Int. Cl.³ .................................... C07D 459/00
[52] U.S. Cl. ........................... 546/70; 424/256
[58] Field of Search .......................... 546/70

[56] References Cited

U.S. PATENT DOCUMENTS 3,770,724 11/1973 Warnant et al. ............ 260/239.3 P
4,089,856 5/1978 Szántay et al. .................. 546/70
4,315,011 2/1982 Szántay et al. .................. 424/256

Primary Examiner—Paul M. Coughlan, Jr.
Assistant Examiner—D. B. Springer

[57] ABSTRACT

The invention relates to a new process for the preparation of alkoxyvincaminic acid esters of the formula (I)

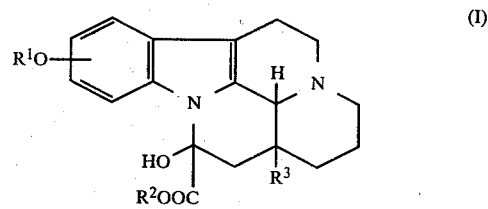

and/or alkoxyapovincaminic acid esters of the formula (II)

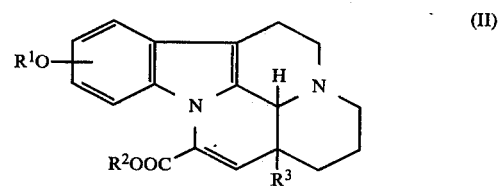

wherein $R^1$, $R^2$ and $R^3$ independently stand for alkyl groups having from one to 6 carbon atoms.

The compounds of the formulae (I) and (II) are pharmaceutically active, thus some of them show psychostimulant activity.

4 Claims, No Drawings

1α-ETHYL-1β-(2'-ALKOXY CARBONYL-2'-HYDROXYIMINOETHYL)-10-METHOXY 1,2,3,4,6,7,12,12β-OCTAHYDROINDOLO(2,3A)-QUINOLIZINES

The invention relates to a new process for the preparation of alkoxyvincaminic acid esters of the formula (I)

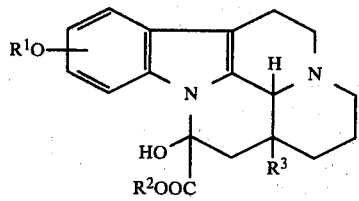

(I)

and/or alkoxyapovincaminic acid esters of the formula (II)

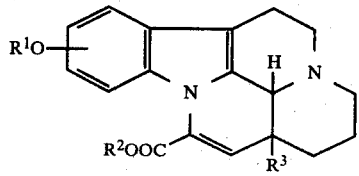

(II)

wherein
$R^1$, $R^2$ and $R^3$ independently stand for alkyl groups having from one to 6 carbon atoms,
and epimers, racemates, optical antipodes and pharmaceutically acceptable acid addition salts thereof, which comprises
reacting a racemic or optically active halooctahydroindoloquinolizine of the formula (III)

(III)

or halohomoeburnane of the formula (IV)

(IV)

wherein
$R^3$ has the same meaning as defined above,
$R^4$ is alkyl having from one to 6 carbon atoms,
X and is halogen,
or a salt thereof with an alkanolate of the formula $R^1$-OMe, wherein
$R^1$ has the same meaning as defined above, and
Me stands for an alkali metal,
in the presence of a catalyst; or reacting a racemic or optically active alkoxyindole derivative of the formula (V)

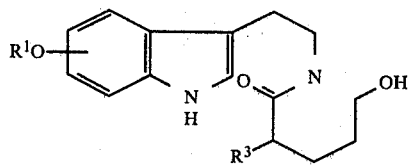

(V)

wherein $R^1$ and $R^3$ have the same meaning as defined above, or a salt thereof with a phosphorus oxyhalide, treating an alkoxyhexahydroindoquinolizinium salt of the formula (VIa)

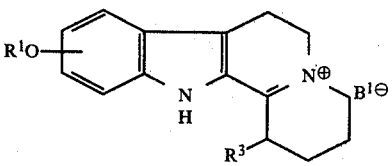

(VIa)

wherein
$R^1$ and $R^3$ are the same as defined above, and
$B^1$ is an acid residue,
obtained, with a base, reacting a hexahydroindoloquinolizine of the formula (VIb)

(VIb)

wherein $R^1$ and $R^3$ are the same as defined above, obtained with an acrylic acid ester of the formula $CH_2=CH-COOR^4$, wherein $R^4$ has the same meaning as defined above, saturating an alkoxyhexahydroindoloquinolizinium ester of the formula (VII)

(VII)

wherein
$R^1$, $R^3$ and $R^4$ are as defined above, and
$B^2$ is an acid residue,
obtained and separating the epimeric mixture obtained, and subsequently treating an octahydroindoloquinolizine ester of the formula (VIII)

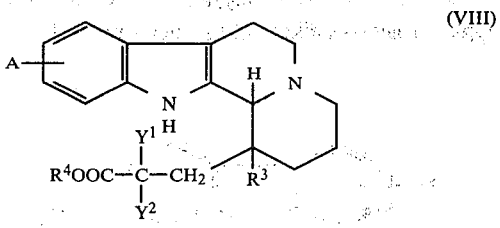

(VIII)

in which
$R^2$ and $R^3$ have the same meaning as defined above,
A is a group $R^1O—$, in which $R^1$ is as defined above,
$Y^1$ and $Y^2$ stand for hydrogen,
or a salt thereof, prepared starting from compounds of the formulae (III), (IV) or (VII), with a strong base, oximating an alkoxyhomoeburnane of the formula (IX)

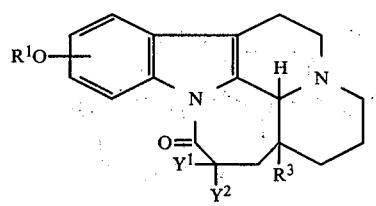

(IX)

wherein
$R^1$ and $R^3$ have the same meaning as defined above, and $Y^1$ and $Y^2$ stand for hydrogen, obtained or a salt thereof, and reacting an alkoxyhomoeburnane of the formula (IX) obtained, in which $R^1$ and $R^3$ have the same meaning as defined above and $Y^1$ and $Y^2$ together form an =NOH group,
with an alkanol of the formula $R^2$—OH, in which $R^2$ is as defined above, in the presence of a strong concentrated acid, to yield compounds of the formula (II), wherein $R^1$, $R^2$ and $R^3$ have the same meaning as defined above; or
reacting an alkoxyhomoeburnane of the formula (IX), in which $R^1$ and $R^3$ are as defined above and $Y^1$ and $Y^2$ together form an =NOH group, or a salt thereof with an alkanol of the formula $R^2$—OH, wherein $R^2$ is as defined above, in the presence of an alkaline reactant; or
reacting a racemic or optically active halohomoeburnaneoxime of the formula (X)

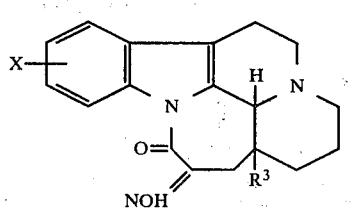

(X)

in which
$R^3$ is as defined above, and
X stands for halogen,
or a salt thereof, if $R^1$ and $R^2$ are identical, directly, or after converting same into an octahydroindoloquinolizine ester of the formula (VIII), in which $R^2$ and $R^3$ are as defined above, A is halogen and $Y^1$ and $Y^2$ together form an =NOH group, by reacting with an alkanol of the formula $R^2$—OH, in which $R^2$ has the same meaning as defined above, with an alkanolate of the formula $R^1$—OMe, in which $R^1$ and Me are as defined above, in the presence of a catalyst,
and subsequently treating an octahydroindoloquinolizine ester of the formula (VIII), in which $R^2$ and $R^3$ have the same meaning as defined above, A stands for a group $R^1O—$, in which $R^1$ is as defined above and $Y^1$ and $Y^2$ together form an =NOH group, prepared from a compound of the formula (IX), in which $Y^1$ and $Y^2$ together form an =NOH group and $R^1$ and $R^2$ have the same meaning as defined above, by an alkaline agent or from a compound of the formula (X) or (VIII), in which A is halogen and $Y^1$ and $Y^2$ together form an =NOH group and $R^2$ and $R^3$ have the same meaning as defined above, as described above, or a salt thereof, with a concentrated strong acid to give compounds of the formula (II), or with a dilute acid to give a mixture of compounds of formulae (I) and (II), separating compounds of the formula (I) from the above mixture,
and if desired, converting compounds of the formulae (I) and/or (II) into each other, esterifying, resolving same or converting them into pharmaceutically acceptable acid addition salts thereof, providing that resolution can be carried out in any stage of the reaction.

The compounds of the formulae (I) and (II) are pharmaceutically active, thus some of them show psychostimulant activity. The compounds can further be used as starting materials in the synthesis of potent vasodilators, e.g. apovincinol trimethoxybenzoyl ester (see Hungarian Patent specification No. 170,180). Certain representatives of these compounds, e.g. (+)-11-methoxy-vincamine [(+)-vincine] and (+)-11-methoxy-apovincamine [(+)-apovincine] are native materials, which are present in plants. (+)-Vincine can be isolated from plants as described in Pharm. Acta. Helv. 35, 96 (1960) and Coll. Czech. Chem. Somm. 26, 867 (1961).

In the published German Patent specification No. 2,458,164 there are disclosed some cis-vincaminic acid and cis-apovincaminic acid esters monosubstituted in the A-ring, where the substituents include alkoxy groups, only the preparation of 10-methoxy compound is exemplified. Moreover, the cumbersome, multistep synthesis starts from materials and reactant which are difficult to access.

According to the new synthesis disclosed in the present application the desired end product can be prepared from readily available, simple starting materials by simple reaction steps, through new intermediates, with an excellent yield.

In the definition of $R^1$, $R^2$, $R^3$ and $R^4$ the term "alkyl having from one to six carbon atoms" is used to define straight or branched chained alkyl groups having from one to 6 carbon atoms, e.g. methyl, ethyl, n-propyl, isopropyl, n-butyl, sec-butyl, tert-butyl, n-pentyl, isopentyl, n-hexyl and isohexyl, preferably methyl or ethyl.

In the definition of X and A the term "halogen" refers to fluorine, chlorine, bromine or iodine, preferably chlorine or bromine, more preferably bromine.

$B^1$ and $B^2$ as an acid residue may stand for the residue of any organic or preferably inorganic acid, e.g. a halide, such as chloride or preferably perhalogenate, e.g. perchlorate.

The starting compounds of the formula (III) are disclosed in the Hungarian Patent Application RI-675 see U.S. Pat. No. 4,315,011 and in the Hungarian Patent specification No. 177,729, the compounds of the formula (IV) can be prepared according to the British Patent Specification No. 2,036,721, the compounds of the formula (V) according to Tetrahedron 33, 1803 (1977) and the compounds of the formula (XI) according to the Hungarian Patent specification No. 178,702.

The intermediates of the formulae (VIa), (VIb), (VII), (VIII) and (IX) are new.

In the reaction of the compounds of the formulae (III), (IV), (VIII) (A=halogen, $Y^1$ and $Y^2$ together=$=$NOH) and (X), respectively with the compounds of the formula $R^1$—OMe as a catalyst an inorganic salt containing a monovalent copper ion may be employed. The catalysts include e.g. cuprous iodid, cuprous rhodanide, cuprous chloride, cuprous bromide, etc., preferably cuprous iodide. As a solvent for the reaction preferably an alkanol of the formula $R^1$—OH corresponding to the alkanolate of the formula $R^1$—OMe and dimethyl formamide or dimethyl acetamide or 2,4,6-collidine or 2,6-lutidine or pyridine, etc., preferably dimethyl formamide may be employed. The reaction preferably is performed between 25° C. and 140° C. Though the amount of the reactants is not critical, generally 3 to 15 moles of the alkanolates of the formula $R^1$—OMe and 0.5 to 4 moles of the cuprous salt catalysts are used calculated for one mole of the compounds of the formulae (III), (IV), (VIII) and (X), respectively.

The compounds of the formula (V) are preferably reacted with phosphorus oxychloride as a phosphorus oxyhalide. The reaction is preferably carried out in the excess of phosphorus oxychloride, which serves as a solvent as well, at the boiling temperature of the mixture.

The compounds of the formula (VIa) can be treated with an inorganic base, preferably an aqueous solution of an alkali metal hydroxide, e.g. sodium hydroxide or potassium hydroxide, in a reaction inert, water-immiscibel organic solvent, such as an optionally halogenated aliphatic or aromatic hydrocarbon, preferably dichloromethane. The compounds of the formula (VIb) obtained by this reaction if desired, can further be reacted with a compound of the formula $CH_2=CH$—$COOR^4$ without elimination.

The saturation of the compounds of the formula (VII) can be accomplished with a chemical reducing agent, preferably a metal hydride, e.g. lithiumaluminium hydride or preferably sodium borohydride, or with catalytically activated hydrogen, where preferably palladium-on-charcoal is employed as a catalyst. The saturation is performed in an inert organic solvent, preferably an aliphatic alcohol, more preferably methanol, at room temperature. As a result, a mixture of the corresponding 12bα- and 12bβ-epimers is obtained. The epimers may be separated for example by preparative thin layer chromatography and the subsequent steps of the process can be carried out also with the 12bα- and 12bβ-epimers, respectively.

As a strong base for treating the compounds of the formula (VIII) (A=$R^1O$, $Y^1=Y^2=H$) for example an alkali metal tert-alcoholate, preferably sodium tert-butylate can be employed. The reaction is carried out in an inert organic solvent, e.g. aromatic hydrocarbon, preferably toluene.

The oximation of the compounds of the formula (IX) ($Y^1=Y^2=H$) is carried out with a tert-alkyl nitrite, preferably tert-butyl nitrite, in the presence of a strong base, such as an alkali metal tert-alcoholate, e.g. potassium tert-butylate, in an inert organic solvent, e.g. an aromatic hydrocarbon, preferably toluene.

When treating compounds of the formula (VIII) (A=$R^1O$, $Y^1=Y^2=H$) with a strong base or oximating compounds of the formula (IX) ($Y^1=Y^2=H$) the humidity is preferably excluded and the reactions are preferably performed at room temperature.

For treating a mixture of the compounds of the formula (IX), in which $Y^1$ and $Y^2$ together form an $=$NOH group and alkanols of the formula $R^2$—OH or compounds of the formula (VIII), in which A stands for a group $R^1O$ and $Y^1$ and $Y^2$ together form an $=$NOH group and $R^2$ and $R^3$ are as hereinabove defined, with a strong concentrated acid, preferably sulfuric acid, organic sulfonic acids, e.g. benzenesulfonic acid, toluenesulfonic acid, preferably p-toluenesulfonic acid may be employed. The reaction is generally performed in a solvent, thus in an alcohol of the formula $R^2$—OH or an inert organic solvent, such as aromatic hydrocarbon, preferably toluene.

As an alkaline agent for the reaction of the compounds of the formula (IX) ($Y^1$ and $Y^2$ together=$=$NOH) or (X) with the compounds of the formula $R^2OH$ for example an alkali metal alcoholate optionally formed in situ in the reaction mixture, preferably sodium methylate can be employed. The reaction is preferably performed at about the boiling temperature of the reaction mixture.

The compounds of the formula (VIII), in which A stands for an $R^1O$ group and $Y^1$ and $Y^2$ together form an $=$NOH group are preferably treated with a 5% aqueous sulfuric acid solution as a dilute aqueous acid.

The compounds of the formula (I) and (II) can be separated for example by crystallization from appropriately selected solvent(s) or by preparative thin layer chromatography.

The compounds of the formulae (I) and (II) can be converted into each other by dehydration and water addition, respectively.

The esterification of the compounds of the formulae (I) and (II), their conversion into the corresponding salts as well as the resolution of the end products and intermediates are performed in a manner known in the art.

Further details of the invention are to be found in the following examples which are intended for illustration and not for limitation.

EXAMPLE 1

(±)-1α-Ethyl-1β-(2'-methoxycarbonylethyl)-9-methoxy-1,2,3,4,6,7,12,12bα-octahydroindolo[2,3-a]quinolizine 0.24 g (10.4 mmoles) of sodium metal are dissolved in 3 ml of absolute methanol, under nitrogen atmosphere. 5 ml of absolute dimethyl formamide and 0.50 g (2.62 mmoles) of cuprous iodide are added to the solution followed by the addition of 0.40 g (0.95 mmoles) of (±)-1α-ethyl-1β-(2'-methoxycarbonylethyl)-9-bromo-1,2,3,4,6,7,12,12bα-octahydroindolo[2,3-a]quinolizine (prepared according to the Hungarian Patent Application No. RI-675). The reaction mixture is stirred at 100° C., under nitrogen atmosphere for 2 hours.

Upon cooling the mixture is poured onto 15 ml of ice water, shaken with 10 ml of ethyl acetate and the inorganic precipitate is filtered off. The organic phase is separated and the aqueous phase is extracted with three 5 ml portions of ethyl acetate. The combined organic phases are shaken with 10 ml of water, dried with magnesium sulfate, filtered and from the filtrate the solvent is distilled off in vacuo. 0.39 g of an oily product are obtained as distillation residue which is then dissolved in 1.5 ml of methanol, the pH of the solution is adjusted to 4 with hydrochloric acid in methanol, the precipitated crystals are filtered off, washed with 0.5 ml of methanol and dried.

0.20 g of the title compound are obtained as a hydrochloride.

Yield: 52%.

Melting point: 234° to 236° C. (methanol).

IR spectrum (KBr): 3380 (indole-NH); 1728 (ester CO); 1620 cm$^{-1}$ (aromatic).

Mass spectrum m/e: (%): 370 (M$^+$, $C_{22}H_{30}N_2O_3$, 62); 369 (57); 355 (6.9); 340 (5.1); 339 (8.7); 311 (3); 297 (100); 283 (4.9); 267 (7.3); 241 (4.9); 228 (11); 227 (23); 215 (12); 214 (9.5); 200 (25); 199 (15); 186 (6.4).

$^1$H-NMR spectrum (CDCl$_3$): δ=7.68 (1H, indole-NH); 7.23–6.74 (3H, m, aromatic); 3.83 (3H, s, OCH$_3$); 3.57 (3H, s, CO$_2$CH$_3$); 3.32 (1H, 12b—H); 1.12 (3H, t, CH$_2$C$\underline{H}_3$).

EXAMPLE 2

1-(Ethyl-1-[2'-methoxycarbonylethyl]-9-methoxy-1,2,3,4,6,7-hexahydro-12H-indolo[2,3-a]quinolizin-5-ium perchlorate 0.5 g (1.3 mmoles) of 1-ethyl-9-methoxy-1,2,3,4,6,7-hexahydro-12H-indolo[2,3-a]quinolizin-5-ium perchlorate [Heterocycles 6, 321 (1977)] in 10 ml of dichloromethane are stirred with 9.3 ml of a 2.5% aqueous sodium hydroxide solution for 5 minutes.

The organic phase is separated, dried with potassium carbonate, filtered, to the filtrate 0.8 ml of methylacrylate are added and the solution is allowed to stand at room temperature for one day. From the solution the solvent is distilled off in vacuo, the oily evaporation residue is dissolved in 5 ml of methanol, the pH of the solution is adjusted to 4 with a 70% perchloric acid solution, the precipitated crystals are filtered off, washed with 1 ml of methanol and dried.

0.52 g of the title compound are obtained.

Yield: 85%.

Melting point: 173° to 174° C. (methanol).

IR spectrum (KBr): 3400 (indole-NH); 1716 (ester CO); 1628 (C=N); 1595 cm$^{-1}$ (aromatic).

EXAMPLE 3

(±)-1α-Ethyl-1β-(2'-methoxycarbonylethyl)-9-methoxy-1,2,3,4,6,7,12,12bα-octahydro-indolo[2,3-a]quinolizine and (±)-1α-ethyl-1β-(2'-methoxycarbonylethyl)-9-methoxy-1,2,3,4,6,7,12,12bβ-octahydro-indolo[2,3-a]quinolizine To a suspension of 0.40 g (0.87 mmoles) of 1-ethyl-1-(2'-methoxycarbonylethyl)-9-methoxy-1,2,3,4,6,7-hexahydro-12H-indolo[2,3-a]quinolizin-5-ium perchlorate (Example 2) in 10 ml of methanol 25 mg of sodium borohydride are added at 0° C., under continuous stirring, and stirring is continued for further 35 minutes. The pH of the solution is then adjusted to 7.5 with glacial acetic acid, and the solvent is eliminated by distillation in vacuo. The oily distillation residue is dissolved in 15 ml of dichloromethane and the solution is shaken with 5 ml of a 5% aqueous sodium carbonate solution. The organic phase is separated, dried with solid, anhydrous magnesium sulfate, filtered and from the filtrate the solvent is distilled off in vacuo. 0.30 g of an oily product are obtained which are then further purified by preparative thin layer chromatography (Kieselgel PF$_{254+366}$, a 14:3 mixture of benzene and methanol, elution with acetone).

From the layer having a greater R$_f$-value 0.12 g of an oily product are obtained, which are crystallized from methanol.

Thus 0.06 g of the trans-12bβH title compound are obtained.

Yield: 18.6%

Melting point: 103° to 104° C. (methanol).

IR spectrum (KBr): 3350 (indole-NH); 1705 (ester CO); 1620 cm$^{-1}$ (aromatic).

Mass spectrum m/e (%): 370 (M$^+$, $C_{22}H_{30}N_2O_3$, 80); 369 (72); 355 (10); 339 (9.4); 311 (2.7); 297 (100); 295 (7.3); 283 (5.1); 267 (7.3); 241 (4.5); 227 (27); 215 (15); 201 (9.0); 200 (27); 199 (16).

From the zone having a lower R$_f$-value after elution 0.17 g of an oily product are obtained. The oil is dissolved in 1 ml of methanol, the pH of the solution is adjusted to 4 by hydrochloric acid in methanol, the precipitated crystals are filtered off, washed with 0.5 ml of methanol and dried. 0.12 g of the 12bαH-ester title compound are obtained as a hydrochloride, which has the same physico-chemical characteristics as the product of Example 1.

Yield: 34%.

EXAMPLE 4

(−)-1α-Ethyl-1β-(2'-methoxycarbonylethyl)-10-methoxy-1,2,3,4,6,7,12,12bα-octahydroindolo[2,3-a]quinolizine hydrochloride 0.24 g (10.4 mmoles) of sodium metal are dissolved in 3 ml of absolute methanol under exclusion of humidity, in nitrogen stream. When dissolution is complete, 5 ml of absolute dimethyl formamide and 0.50 g (2.6 mmoles) of freshly prepared cuprous iodide (G. Brauer: Handbuch der Preparativen Anorganischen Chemie, 1954, p. 753) are added to the solution, under continuous stirring, followed by the addition of 0.40 g (1.03 mmoles) of (+)-3α, 17α-11-bromo-14-oxo-E-homo-eburnane (Hungarian Patent specification No. 177,728). The reaction mixture is stirred in nitrogen atmosphere, in an outer bath having a temperature of 110° C. for 2.5 hours.

After cooling the mixture is poured onto 20 ml of ice water, shaken with 20 ml of ethyl acetate, and the precipitated inorganic substance is filtered off and the substance on the filter is washed with 10 ml of ethyl acetate. The filtrate is extracted with further three 10 ml portion of ethyl acetate, the combined organic phases are shaken with 15 ml of water and dried over solid, anhydrous magnesium sulfate. After filtration and evaporation of the filtrate in vauco 0.40 g of an oily product are obtained. The product is dissolved in 5 ml of acetonitrile, the pH of the solution is adjusted to 4 with hydrochloric acid in methanol and the precipitated (−)-1α-ethyl-1β-(2'-methoxy-carbonyl-ethyl)-10-methoxy-1,2,3,4,6,12,12bα-octahydro-indolo[2,3-a]quinolizine hydrochloride is washed with 2 ml of acetonitrile.

235 mg of the title ester are obtained.

Yield: 56%.

Melting point: 225° to 226° C. (acetonitrile).

IR spectrum (KBr): 3400 (indole-NH); 1742 (ester CO); (aromatic).

Mass spectrum m/e (%): 370 (M$^+$, $C_{22}H_{30}N_2O_3$, 68); 369 (69); 355 (14); 339 (14); 311 (2.5); 297 (100); 283

(4.8); 267 (7.3); 228 (8); 227 (22); 215 (14); 200 (30); 199 (17); 186 (9.1).

$^1$H-NMR spectrum (CDCl$_3$): δ=7.67 (1H, indole-NH); 7.36–6.70 (3H, m, aromatic); 3.84 (3H, s, 10-OCH$_3$); 3.57 (3H, s, COOCH$_3$); 3.32 (1H, 12b-H); 1.13 (3H, t, CH$_2$CH$_3$).

$[α]_D^{20}$ = −73.1°; $[α]_{546}^{20}$ = −85.3° (c=0.82, a 4:1 mixture of dichloromethane and methanol).

EXAMPLE 5

1-Ethyl-10-methoxy-1,2,3,4,6,7-hexahydro-12H-indolo[2,3-a]quinolizinium perchlorate 1.05 g (3.49 mmoles) of N-(6-methoxy-indolyl-3-ethyl)-α-ethyl-δ-valerolactame [Tetrahedron 33, 1803 (1977)] in 25 ml of freshly distilled phosphorus oxychloride, under nitrogen stream are boiled for two hours. From the reaction mixture the excess of phosphorus oxychloride is distilled off in vacuo, the residue is dissolved in 50 ml of dichloromethane, the solution is shaken with 10 ml of a 5% aqueous ammonium hydroxide solution, the organic phase is washed with 5 ml of water, dried with solid, anhydrous magnesium sulfate and filtered. From the filtrate the solvent is distilled off in vacuo, the residual oil is dissolved in 3 ml of methanol and the solution is acidified to pH=5–6 with a 70% aqueous perchloric acid solution. The precipitated substance is filtered off, washed with 1 ml of methanol and dried.

850 mg of the crude title compound are obtained.

Yield: 63.5%.

Melting point: 200° to 213° C.

The crude product is recrystallized from 5 ml of methanol. 605 mg of the title compound are obtained as a yellow, crystalline substance.

Yield: 45.4%.

Melting point: 220° to 222° C.

IR spectrum (KBr): 3250, 1620, 1565, 1540, 1260 cm$^{-1}$.

EXAMPLE 6

1-Ethyl-1-(2'methoxycarbonylethyl)-10-methoxy-1,2,3,4,6,7-hexahydro-12H-indolo[2,3-a]quinolizinium perchlorate A mixture of 121 mg (0.3 mmoles) of 1-ethyl-10-methoxy-1,2,3,4,6,7-hexahydro-12H-indolo[2,3-a]quinolizinium perchlorate (Example 5), 7.5 ml of water, 0.5 ml of a 10% aqueous sodium hydroxide solution and 3 ml of dichloromethane is stirred at room temperature for 10 minutes. The organic phase is separated, dried with solid, anhydrous potassium carbonate, filtered, to the filtrate 0.2 ml of acrylic acid methyl ester are added and the mixture is allowed to stand for 20 hours. From the reaction mixture the excess reactant and the solvent are eliminated by distillation in vacuo. 125 mg oily distillation residue are obtained, which are then dissolved in 1 ml of methanol and treated with a 70% aqueous perchloric acid solution. 52 mg of the title perchlorate are obtained.

Yield: 37%.

Melting point: 125° to 127° C.

IR spectrum (KBr): 3280, 1720, 1620, 1580, 1520, 1345, 1080 cm$^{-1}$.

EXAMPLE 7

(±)-1α-Ethyl-1β-(2'-methoxycarbonylethyl)-10-methoxy-1,2,3,4,6,7,12,12bα-octahydroindolo[2,3-a]quinolizine and (±)-1α-ethyl-1β-(2'-methoxycarbonylethyl)-10-methoxy-1,2,3,4,6,7,12,12bβ-octahydroindolo[2,3-a]quinolizine 52 mg (0.11 mmoles) of 1-ethyl-1-(2'-methoxycarbonylethyl)-10-methoxy-1,2,3,4,6,7-hexahydro-12H-indolo[2,3-a]quinolizinium perchlorate (Example 6) are dissolved in 10 ml of methanol and to the solution 8 mg of sodium borohydride are added. The mixture is stirred for 30 minutes, one drop of acetic acid is added and the methanol is distilled off. The residue is partitioned between 3.5 ml of dichloromethane and 1 ml of a 10% aqueous sodium carbonate solution. After separation the organic layer is dried with solid, anhydrous magnesium sulfate, filtered and the filtrate is evaporated. As an evaporation residue 50.3 mg of a product mixture are obtained. After separation by preparative thin layer chromatography an (a) and a (b) product is obtained (R$_f$a>R$_f$b, a 8:2 mixture of benzene and methanol).

The product (a) is 9.6 mg of (±)-1α-ethyl-1β-(2'-methoxycarbonylethyl)-10-methoxy-1,2,3,4,6,7,12,12bβ-octahydroindolo[2,3-a]quinolizine.

Yield: 23%.

Melting point: 120° to 123° C.

IR spectrum (KBr): 1710, 1630, 1460, 1440, 1265, 1150, 1030 cm$^{-1}$.

Mass spectrum m/e (%): 370 (M$^+$, 59); 369 (61); 297 (100); 227 (23); 215 (10); 200 (37); 199 (20); 107 (16).

As a product (b) 13 mg of (±)-1α-ethyl-1β-(2'-methoxycarbonylethyl)-10-methoxyl-1,2,3,4,6,7,12,12bα-octahydroindolo[2,3-a]quinolizine hydrochloride are obtained.

Yield: 29%.

Melting point: 195° to 196° C.

The IR and Mass Spectrum data of the compound are identical with those given in Example 4.

EXAMPLE 8

(−)-1α-Ethyl-1β-(2'-methoxycarbonylethyl)-8-methoxy-1,2,3,4,6,7,12,12bα-octahydroindolo[2,3-a]quinolizine 0.30 g (13.0 mmoles) of sodium metal are dissolved in 3.7 ml of absolute methanol under exclusion of humidity, in a continuous nitrogen stream. When the dissolution is complete, 6.25 ml of absolute dimethyl formamide, 0.625 g (3.28 mmoles) of freshly prepared cuprous iodide and subsequently 0.50 g (1.3 mmoles) of (+)-3(S),17(S)-9-bromo-14-oxo-E-homo-eburnane (Hungarian Patent specification No. 177,778) are added. The reaction mixture is kept in nitrogen atmosphere on an outer bath of 110° C.

Upon cooling the mixture is poured onto 25 ml of ice water, shaken with 15 ml of ethyl acetate, the precipitated inorganic material is filtered off and the solid is washed with 10 ml of ethyl acetate. The filtrate is extracted with four further 8 ml portions of ethyl acetate, the combined organic phases are shaken with 10 ml of water. The organic phase is dried on solid, anhydrous magnesium sulfate, filtered, evaporated in vacuo and the evaporation residue weighing 0.54 g (oil) is dissolved in 2.5 ml of acetonitrile. The pH of the solution is adjusted to 5, the precipitated substance is filtered off and washed with 1 ml of acetonitrile.

0.25 g of the hydrochloride of the title compound are obtained.

Yield: 48.7%.

Melting point: 241° to 242° C. (acetonitrile).

A portion of the hydrochloride is converted into the corresponding free base by dissolving it in dichloromethane and shaking the solution with a 5% aqueous sodium hydrogencarbonate solution. The organic phase is separated, dried and the solvent is eliminated.

The obtained oily product is crystallized from methanol. The title compound is obtained, melting at 160° to 162° C.

$[\alpha]_D^{20} = -111.8°$ and $[\alpha]_{546}^{20} = -133.6°$ (c=1.01; dichloromethane).

The hydrochloride of the title compound can be characterized by the following spectrum data:

IR spectrum (KBr): 3500 (indole-NH); 1725 (ester CO); 1608, 1580 cm$^{-1}$ (aromatic).

Mass spectrum m/e (%): 370 (M+, $C_{22}H_{30}N_2O_3$, 72); 369 (76); 355 (9); 339 (9); 327 (0.8); 311 (1.5); 297 (100); 283 (3); 281 (3); 267 (3); 251 (1.5); 241 (3); 227 (22); 215 (11); 200 (29); 185 (9).

EXAMPLE 9

3(S),17(S)-11-Methoxy-14-oxo-E-homo-eburnane 0.76 g (1.87 mmoles) of (−)-1α-ethyl-1β-(2'-methoxycarbonylethyl)-10-methoxy-1,2,3,4,6,7,12,12bα-octahydroindolo[2,3-a]quinolizine hydrochloride (Example 4) and 0.72 g (7.42 mmoles) of sodium tert-butylate are stirred in 15 ml of absolute toluene, under nitrogen atmosphere, at room temperature for 5 hours. To the reaction mixture 0.8 g of ammonium chloride in 10 ml of water are added, the mixture is stirred for 5 minutes, the organic phase is separated and the aqueous phase is extracted with four 5 ml portions of dichloromethane. The combined organic phases are dried on solid, anhydrous magnesium sulfate, filtered and from the filtrate the solvent is eliminated by distillation in vacuo.

The residual 0.60 g of an oily product is crystallized from 2 ml of methanol. The precipitated crystals are filtered off, washed with 0.5 ml of methanol and dried.

267 mg of the title compound are obtained.

From the mother liquor by preparative layer chromatography (Kieselgel PF$_{254+366}$, a 14:3 mixture of benzene and methanol; R$_f$ starting material <R$_f$ end product; elution with acetone) further 65 mg of the title product can be isolated.

Thus altogether 332 mg of the title compound are obtained.

Total yield: 52.5%.

Melting point: 138° to 140° C. (methanol).

IR spectrum (KBr): 1685 (amide CO); 1600 cm$^{-1}$ (aromatic).

Mass spectrum m/e (%): 338 (M+, $C_{21}H_{26}N_2O_2$, 100); 337 (82); 323 (2); 310 (11); 309 (16); 296 (8); 295 (5); 282 (18); 281 (20); 267 (9); 168 (10).

EXAMPLE 10

(+)-3(S),17(S)-11-Methoxy-14-oxo-15-hydroxyimino-E-homo-eburnane

To a solution of 0.34 g (1.00 mmoles) of 3(S),17(S)-11-methoxy-14-oxo-E-homo-eburnane (Example 9) in 4.6 ml of toluene 0.92 ml of tert-butyl nitrite and 0.29 g of potassium tert-butylate are added in nitrogen atmosphere, whereupon the reaction mixture is stirred at room temperature for 20 minutes.

Thereafter a solution of 0.77 g of ammonium chloride in 5 ml of water is added to the mixture, which is then stirred for 3 minutes. The organic phase is separated, the aqueous phase is extracted with three 5-ml portions of dichloromethane, the combined organic phases are dried on magnesium sulfate, filtered and from the filtrate the solvent is distilled off in vacuo. 0.34 g of an oily product are obtained. The crude product is dissolved in 3 ml of acetonitrile, the pH of the solution is adjusted to 4 by hydrochloric acid in methanol, and the precipitated hydrochloride of the title compound is filtered off, washed with 1 ml of acetonitrile and dried.

185 mg of the title compound are obtained.

Yield: 46%.

Melting point: 228° to 230° C. (acetonitrile, decomp.).

IR spectrum (KBr): 3400 (OH); 1700 (amide CO); 1630 (C=N); 1610 cm$^{-1}$ (aromatic).

Mass spectrum m/e (%): 367 (M+, $C_{21}H_{25}N_2O_3$, 100); 366 (62); 351 (19); 350 (28); 338 (26); 337 (78); 323 (19); 322 (63); 310 (10); 295 (10); 295 (10); 293 (14); 281 (18); 267 (16); 200 (9.4); 199 (13).

$[\alpha]_D^{20} = +125°$; $[\alpha]_{546}^{20} = 175.9°$ (c=0.82; dichloromethane).

EXAMPLE 11

(−)-1α-Ethyl-1β-(2'-methoxycarbonyl-2'-hydroxyiminoethyl)-10-methoxy-1,2,3,4,6,7,12,12bα-octahydroindolo-[2,3-a]quinolizine 0.40 g (1.08 mmoles) of (+)-3(S),17(S)-11-methoxy-14-oxo-15-hydroxyimino-E-homo-eburnane (Example 10) in 5 ml of absolute methanol, in the presence of 0.13 g of sodium methylate are boiled for one hour, under exclusion of humidity.

Upon cooling the sodium methylate is decomposed with acetic acid, and the solution is evaporated to dryness in vacuo. To the residue 2 ml of water are added, the pH is adjusted to 8 by a 1:1 solution of ammonium hydroxide in water, and the mixture is extracted with three 5-ml portions of dichloromethane. The organic phase is dried with solid, anhydrous magnesium sulfate, filtered and with residual 0.35 g of an oily product are dissolved in 1 ml of methanol. The pH of the solution is adjusted to 4 by hydrochloric acid in methanol, the precipitated hydrochloride of the title compound is filtered off, washed with 0.5 ml of methanol and subsequently with 1 ml of ether and dried.

225 mg of the title compound are obtained.

Yield: 47.8%.

Melting point: 221° to 222° C. (methanol).

IR spectrum (KBr): 3300 (NH, OH); 1720 (ester CO); 1618 cm$^{-1}$ (aromatic).

NMR spectrum m/e (%): 399 (M+, $C_{22}H_{29}N_3O_4$, 100); 398 (57); 384 (15); 383 (20); 382 (56); 372 (6.9); 370 (16); 368 (9.2); 340 (25); 323 (13); 322 (24); 308 (8.9); 297 (36); 267 (13).

Optical rotatory power of the base: $[\alpha]_D^{20} = -95.2$; $[\alpha]_{546}^{20} = -121.1°$ (c=0.64; chloroform).

EXAMPLE 12

(−)-1α-Ethyl-1β-(2'-methoxycarbonyl-2-hydroxyiminoethyl)-10-methoxy-1,2,3,4,6,7,12,12bα-octahydroindolo-[2,3-a]quinolizine 61 g (26.5 mmoles) of sodium metal are dissolved in 765 ml of absolute methanol under exclusion of water, in nitrogen stream. When the dissolution is complete, 6.75 ml of absolute dimethyl formamide, 1.275 g (6.63 mmoles) of freshly prepared cuprous iodide and subsequently a solution of 0.93 g (2.24 mmoles) of (+)-3(S),17(S)-11-bromo-14-oxo-15-hydroxyimino-E-homo-eburnane (Hungarian Patent specification No. 178,702) in 6 ml of absolute dimethyl formamide are added. The reaction mixture is stirred under nitrogen atmosphere, at 110° C. for 3 hours.

Upon cooling the mixture is poured onto 25 ml of ice water, the pH of the solution is adjusted to 8 by acetic acid, 25 ml of ethyl acetate are added, the mixture is shaken and the precipitated inorganic substance is filtered off. From the filtrate the organic phase is separated by filtration and the aqueous phase is extracted with three 10-ml portions of ethyl acetate. The combined ethyl acetate phase is shaken with two 15-ml portions of water, dried with solid, anhydrous magnesium sulfate, filtered and from the filtrate the solvent is eliminated in vacuo. The residual 0.59 g of an oily product are dissolved in 2 ml of methanol. The pH of the solution is adjusted to 4 by hydrochloric acid in methanol, the precipitated substance is filtered off, washed with 0.5 ml of methanol and dried.

0.38 g of the title compound are obtained as a hydrochloride.

Yield: 38.7%.

Melting point: 221° to 222° C. (methanol).

IR spectrum (KBr): 3300 (NH, OH); 1720 (ester CO); 1618 cm$^{-1}$ (aromatics).

Mass spectrum m/e (%): 399 (M+, $C_{22}H_{29}N_3O_4$, 100); 398 (57); 384 (15); 383 (20); 382 (56); 372 (6.9); 370 (16); 368 (9.2); 340 (25); 323 (13); 322 (24); 308 (8.9); 297 (36); 267 (13).

The optical rotatory power of the base: $[\alpha]_D^{20} = -95.2$; $[\alpha]_{546}^{20} = -121.1°$ (c=0.64; chloroform).

EXAMPLE 13

1α-Ethyl-1β-(2'-methoxycarbonyl-2'-hydroxyiminoethyl)-10-bromo-1,2,3,4,6,7,12,12bα-octahydroindolo[2,3-a]-quinolizine 0.20 g (0.48 mmoles) of (+)-3(S),17(S)-11-bromo-14-oxo-15-hydroxyimino-E-homo-eburnane (Hungarian Patent specification No. 178,702) in 2 ml of absolute methanol, in the presence of 60 mg of sodium methylate are stirred for one hour, under exclusion of humidity.

The sodium methylate is decomposed with acetic acid (pH=7), and the solvent is distilled off in vacuo. The oily distillation residue is dissolved in 5 ml of dichloromethane and the solution is extracted with 1 ml of a 5% aqueous sodium carbonate solution. The organic phase is separated, dried with solid, anhydrous magnesium sulfate, filtered and from the filtrate the solvent is distilled off in vacuo. 0.16 g of an oily product are obtained. The crude product is crystallized from 1 ml of methanol to yield 0.12 g of the title compound.

Yield: 56%.

Melting point: 191° to 193° C. (methanol).

IR spectrum (KBr): 3400 (NH, OH); 1698 cm$^{-1}$ (ester CO).

Mass spectrum m/e (%): 447 (M+, 100, $C_{21}H_{26}N_3O_3Br$); 446 (41); 430 (51); 417 (12); 415 (10); 388 (18); 370 (14); 345 (24); 289 (12); 275 (43); 263 (27); 262 (41); 248 (59); 247 (40); 234 (12).

EXAMPLE 14

1α-Ethyl-1β-(2'-methoxycarbonyl-2'-hydroxyiminoethyl)-10-methoxy-1,2,3,4,6,7,12,12b α-octahydroindolo-[2,3-a]quinolizine 84 mg (3.65 mmoles) of sodium metal are dissolved in 1.0 ml of methanol, under nitrogen atmosphere and exclusion of humidity. When dissolution is complete, 1.8 ml of absolute dimethyl formamide, 0.175 g (0.9 mmoles) of cuprous iodide and 0.14 g (0.31 mmole) of 1α-ethyl-1β-(2'-methoxycarbonyl-2'-hydroxyiminoethyl)-10-bromo-1,2,3,4,6,7,12,12b α-octahydroindolo[2,3-a]quinolizine (Example 13) are added and the reaction mixture is stirred at 110° C., under nitrogen atmosphere for 3.5 hours.

Thereafter the mixture is poured onto 10 ml of water, the pH of the solution is adjusted to 8 by acetic acid, 5 ml of ethyl acetate are added, it is shaken and the precipitated inorganic substance is filtered off. From the filtrate the organic phase is separated, the aqueous phase is extracted with three 2-ml portions of ethyl acetate. The combined organic phases are shaken with two 1-ml portions of water, dried on solid, anhydrous magnesium sulfate, filtered and from the filtrate the solvent is distilled off in vacuo. 70 mg of an oily product are obtained. The crude product is dissolved in 0.5 ml of methanol, the pH of the solution is adjusted to 4 by hydrochloric acid in methanol, the precipitated substance is filtered off, washed with 0.2 ml of methanol and subsequently with 1 ml of ether and is dried.

40 mg of the title compound are obtained as a hydrochloride.

Yield: 33%.

The physical and chemical characteristics of the product obtained are entirely identical with those of the products of Examples 11 and 12.

EXAMPLE 15

(+)-3(S),17(S)-Vincine and (+)-3(S),17(S)-apovincine 0.24 g (0.55 mmoles) of (−)-1α-Ethyl-1β-(2'-methoxycarbonyl-2'-hydroxyiminoethyl)-10-methoxy-1,2,3,4,6,7,12,12bα-octahydroindolo[2,3-a]quinolizine hydrochloride (Examples 11, 12 and 14) are dissolved in 1 ml of acetic acid and 16 ml of a 5% aqueous sulfuric acid solution. The solution obtained is kept on a bath of 110° C. for three hours.

Under cooling with ice the pH of the solution is adjusted to 8 with an aqueous ammonium hydroxide solution, and the basic solution obtained is extracted with three 5-ml portions of dichloromethane. The combined organic phases are dried on solid, anhydrous magnesium sulfate, filtered and from the filtrate the solvent is distilled off in vacuo. The oily residue, weighing 0.23 g is crystallized from 1 ml of methanol for 24 hours. The precipitated crystals are filtered off, washed with 0.4 ml of cool methanol and dried.

68 mg of (+)-vincine are obtained, which has the same physico-chemical characteristics as an authentic sample of natural origin.

Yield: 32%.

Melting point: 212° C.

Melting point of a sample isolated from plant: 212° C.

Melting point of a mixture: 212° C.

IR spectrum (KBr): 3400 (OH); 1730 (ester CO); 1618 cm$^{-1}$ (aromatic).

Mass spectrum m/e (%): 384 (M+, 100, $C_{22}H_{28}N_2O_4$); 383 (35); 369 (7); 354 (9); 337 (12); 325

(19); 324 (19); 323 (15); 314 (9); 297 (26); 295 (13); 282 (37); 267 (11); 254 (15); 227 (15).

$[\alpha]_D^{20} = +38°$; $[\alpha]_{546}^{20} = +42°$ (c=1.03; pyridine).

The methanolic mother liquor is purified by preparative layer chromatography (Kieselgel PF$_{254+366}$, a 14:3 mixture of benzene and methanol; elution with acetone).

From the zone which has the second greatest R$_f$-value 45 mg (21%) of oily (+)-apovincine can be isolated. The oily product was identified in the form of its D-tartarate. The tartarate is crystallized from 0.5 ml of an acetone/ethyl acetate mixture. The physico-chemical characteristics of the product are entirely identical with these of the apovincine tartarate isolated from plant.

Melting point: 111° C. (a mixture of acetone and ethyl acetate).

IR spectrum (KBr): 3400 (OH); 1718 (ester CO); 1630 (C=C); 1605 cm$^{-1}$ (aromatic).

Mass spectrum m/e (%): 366 (M$^+$, 48, C$_{22}$H$_{26}$N$_2$O$_3$); 365 (7); 351 (P.6); 337 (100); 336 (16); 321 (6); 307 (4); 296 (73); 294 (7); 281 (4).

$[\alpha]_D^{20} = +70.1°$; $[\alpha]_{546}^{20} = +62.6°$ (c=0.6; pyridine).

From the next zone a further 5 mg amount of (+)-vincine is isolated.

Finally from the layer having the lowest R$_f$-value 10 mg of unreacted starting material are isolated.

EXAMPLE 16

(+)-3(S),17(S)-Apovincine 44 mg (0.10 mmoles) of (−)-1α-Ethyl-1β-(2'-methoxycarbonyl-2'-hydroxyiminoethyl)-10-methoxy-1,2,3,4,67,12,12bα-octahydroindolo[2,3-a]quinolizine hydrochloride (Examples 11 and 12) are dissolved in a mixture of 3.75 ml of methanol and 1.35 ml of concentrated sulfuric acid and the solution is heated on water bath for one hour.

After cooling the mixture is poured onto 10 ml of ice water, the pH is adjusted to 8 by a concentrated aqueous ammonium hydroxide solution, under outer cooling and the mixture is extracted with three 5-ml portions of dichloromethane. The combined organic phases are dried with solid, anhydrous magnesium sulfate, filtered and from the filtrate the solvent is eliminated in vacuo. The residual oil, weighing 43 mg is purified by preparative layer chromatography (Kieselgel PF$_{254+366}$, a 14:3 mixture of benzene and methanol; elution with acetone).

20 mg (15%) of (+)-apovincine are obtained. The product is then converted into the corresponding tartarate by 10 mg of D-tartaric acid. The physico-chemical characteristics of the salt are identical with those of the tartarate prepared from (+)-apovincine of natural origin. Melting point: 111° to 113° C. (acetone/ethyl acetate).

$[\alpha]_D^{20} = +70.1°$; $[\alpha]_{546}^{20} = +62.6°$ (c=0.60, pyridine).

10 mg of (+)-apovincine are dissolved in 1 ml of dichloromethane, the pH of the solution is adjusted to 5 by hydrochloric acid in methanol. The solvent is eliminated in vacuo, the residual oily salt is dissolved in 1 ml of warm ethyl acetate, the hydrochloride crystals precipitated upon cooling are filtered off, washed with 0.4 ml of ethyl acetate and subsequently 1 ml of ether and dried.

Melting point of the hydrochloride: 218° to 219° C. (ethyl acetate).

EXAMPLE 17

(+)-3(S),17(S)-Apovincine 30 mg of (0.074 mmoles) of (+)-3(S),17(S)-11-methoxy-14-oxo-15-hydroxyimino-E-homo-eburnane hydrochloride (Example 10) are dissolved in a mixture of 0.9 ml of concentrated sulfuric acid and methanol, which is prepared by adding 1.35 ml of concentrated sulfuric acid to 3.75 ml of absolute methanol dropwise, at 0° C. The solution is then heated on a water bath for 2.5 hours. The progress of the reaction is monitored by thin layer chromatography (absorbent: K6-G silica gel; a 14:3 mixture of benzene and methanol; R$_f$ starting material < R$_f$ end product).

After cooling the mixture is poured onto 8 ml of ice water, the pH is adjusted to 8 with a concentrated aqueous ammonium hydroxide solution, under ice cooling and the mixture is extracted with three 4-ml portions of dichloromethane. The combined organic phases are dried on solid, anhydrous magnesium sulfate, filtered and from the filtrate the solvent is distilled off in vacuo. As a distillation residue 30 mg of an oily product are obtained. The product is dissolved in 2 ml of dichloromethane and the pH of the solution is adjusted to 5 by hydrochloric acid in methanol. The solvent is distilled off in vacuo. The residual oily salt is crystallized from 2 ml of ethyl acetate.

16 mg of the hydrochloride of the title compound are obtained.

Yield: 53.5%.

Melting point: 218° to 219° C.

The further physico-chemical characteristics of the product are identical with those of the (+)-apovincine hydrochloride prepared according to Example 16.

EXAMPLE 18

11-Methoxy-14-oxo-E-homo-eburnane (3β,17α)

Following the procedure described in Example 9 but starting from 1α-ethyl-1β-(2'-methoxycarbonylethyl)-10-methoxy-1,2,3,4,6,7,12,12bβ-octahydroindolo[2,3-a]-quinolizine hydrochloride as a starting material, the title compound is obtained.

EXAMPLE 19

11-Methoxy-14-oxo-15-hydroxyimino-E-homo-eburnane (3β,17α)

Following the procedure described in Example 10 but starting from 11-methoxy-14-oxo-E-homo-eburnane (3β,17α) prepared according to Example 18, the title compound is obtained.

EXAMPLE 20

1α-Ethyl-1β-(2'-methoxycarbonyl-2'-hydroxyiminoethyl)-10-methoxy-1,2,3,4,6,7,12,12bβ-octahydroindolo-[2,3-a]quinolizine Following the procedure described in Example 11 but starting from 11-methoxy-14-oxo-15-hydroxyimino-E-homoeburnane (3β,17α) prepared according to Example 19, the title compound is obtained.

EXAMPLE 21

Trans-vincine (3β,17α) and trans-apovincine (3β,17α)

Following the procedure described in Example 15 but starting from 1α-ethyl-1β-(2'-methoxycarbonyl-2'-hydroxyiminoethyl)-10-methoxy-1,2,3,4,6,7,12,12bβ-

EXAMPLE 22

Trans-apovincine (3β,17α)

Following the procedure described in Example 16 or Example 17 but starting from 11-methoxy-14-oxo-15-hydroxyimino-E-homo-eburnane (3β,17α) or 1α-ethyl-1β-(2'-methoxycarbonyl-2'-hydroxyiminoethyl)-10-methoxy-1,2,3,4,6,7,12,12bβ-octahydroindolo[2,3-a]quinolizine (Example 19 or 20), the title compound is obtained.

Starting from the corresponding 9- or 8-methoxyoctahydroindoloquinolizine prepared in Examples 1 and 8, respectively, and the following the procedure described in Examples 9 to 22, the corresponding cis- or trans- 10- or 9-methoxy-derivatives are prepared.

We claim:

1. A compound of the formula VIII

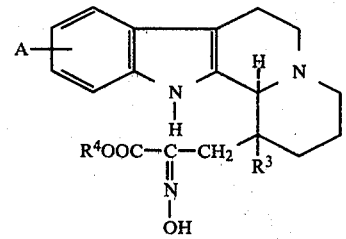

wherein
A is halogen or a group $R^1O-$ in which
$R^1$ is $C_1$ to $C_6$ alkyl, and $R^3$ and $R^4$ are each independently $C_1$ to $C_6$ alkyl, or a pharmaceutically acceptable acid addition salt thereof.

2. The compound defined in claim 1 which is 1α-ethyl-1β-(2'-methoxy-carbonyl-2'-hydroxyiminoethyl)-10-methoxy-1,2,3,4,6,7,12,12b-octahydroindolo(2,3-a)quinolizine.

3. The compound defined in claim 1 which is (−)-1α-ethyl-1β-(2'-methoxy-carbonyl-2'-hydroxyiminoethyl)-10-methoxy-1,2,3,4,6,7,12,12bα-octahydroindolo(2,3-a)quinolizine.

4. The compound defined in claim 1 which is 1α-ethyl-1β-(2'-methoxy-carbonyl-2'-hydroxyiminoethyl)-10-bromo-1,2,3,4,6,7,12,12bα-octahydroindolo(2,3-a)quinolizine.

* * * * *